(12) United States Patent  
Ozyurt et al.

(10) Patent No.: US 11,181,473 B2  
(45) Date of Patent: Nov. 23, 2021

(54) UNDERWATER ANALYSIS DEVICE FOR ANALYZING ABSORPTION CAPACITY OF WATER

(71) Applicant: BAHCESEHIR UNIVERSITESI, Besiktas/Istanbul (TR)

(72) Inventors: Selcuk Ozyurt, Atasehir/Istanbul (TR); Bulent Aydin, Basaksehir/Istanbul (TR); Nil Girgin, Besiktas/Istanbul (TR); Kaan Alper, Cekmekoy/Istanbul (TR); Suleyman Semsioglu, Pendik/Istanbul (TR); Sena Karali, Pendik/Istanbul (TR); Cansin Cokol, Pendik/Istanbul (TR)

(73) Assignee: BAHCESEHIR UNIVERSITESI, Besiktas/Istanbul (TR)

( * ) Notice: Subject to any disclaimer, the term of this patent is extended or adjusted under 35 U.S.C. 154(b) by 55 days.

(21) Appl. No.: 16/618,458

(22) PCT Filed: Jul. 20, 2018

(86) PCT No.: PCT/TR2018/050389  
§ 371 (c)(1),  
(2) Date: Dec. 2, 2019

(87) PCT Pub. No.: WO2019/088953  
PCT Pub. Date: May 9, 2019

(65) Prior Publication Data  
US 2021/0140880 A1    May 13, 2021

(30) Foreign Application Priority Data  
Aug. 3, 2017 (TR) .................................. 2017/11450

(51) Int. Cl.  
*G01N 21/3577* (2014.01)  
*G01N 21/33* (2006.01)  
(Continued)

(52) U.S. Cl.  
CPC ....... *G01N 21/3577* (2013.01); *G01N 21/255* (2013.01); *G01N 21/33* (2013.01); *G01N 33/18* (2013.01); *G01N 2201/0638* (2013.01)

(58) Field of Classification Search  
CPC .. G01N 21/255; G01N 21/33; G01N 21/3577; G01N 2201/0638; G01N 33/18  
See application file for complete search history.

(56) References Cited

U.S. PATENT DOCUMENTS 4,434,364 A * 2/1984 Correa .................. G01V 9/007  
250/253  
5,604,582 A * 2/1997 Rhoads ................. G01J 3/2823  
250/458.1

(Continued)

*Primary Examiner* — David P Porta  
*Assistant Examiner* — Fani Boosalis  
(74) *Attorney, Agent, or Firm* — Lowenstein Sandler LLP

(57) ABSTRACT

The present invention is an underwater analysis device (10) for analyzing absorption capacity of water. Accordingly, the subject matter device is characterized by comprising a body (100) having a sealed first casing (110) which accommodates a sealed illumination window (111); a sealed second casing (130) which accommodates a sealed measurement window (131); a prismatic hollow water chamber (120) provided between said first casing (110) and said second casing (130) and arranged such that a first inlet (121) thereof faces said illumination window (111) and such that a second inlet (122) thereof faces said measurement window (131); said water chamber (120) comprises pluralities water transfer openings (123); said first casing (110) comprises a light emitting unit (113) arranged to emit test light from the illumination window (111) towards the measurement window (131); said second casing (130) comprises a light sensing unit (133) arranged to at least partially receive the test light passing through the water in the water chamber (Continued)

(120) and to embody in a manner generating signal in accordance with the density of the received test light components.

9 Claims, 1 Drawing Sheet

(51) Int. Cl.
    *G01N 33/18*     (2006.01)
    *G01N 21/25*     (2006.01)

(56) References Cited

U.S. PATENT DOCUMENTS

| | | | |
|---|---|---|---|
| 6,507,401 B1* | 1/2003 | Turner | G01N 21/8507 |
| | | | 356/436 |
| 2011/0205536 A1* | 8/2011 | Johnsen | G01N 21/255 |
| | | | 356/326 |

\* cited by examiner

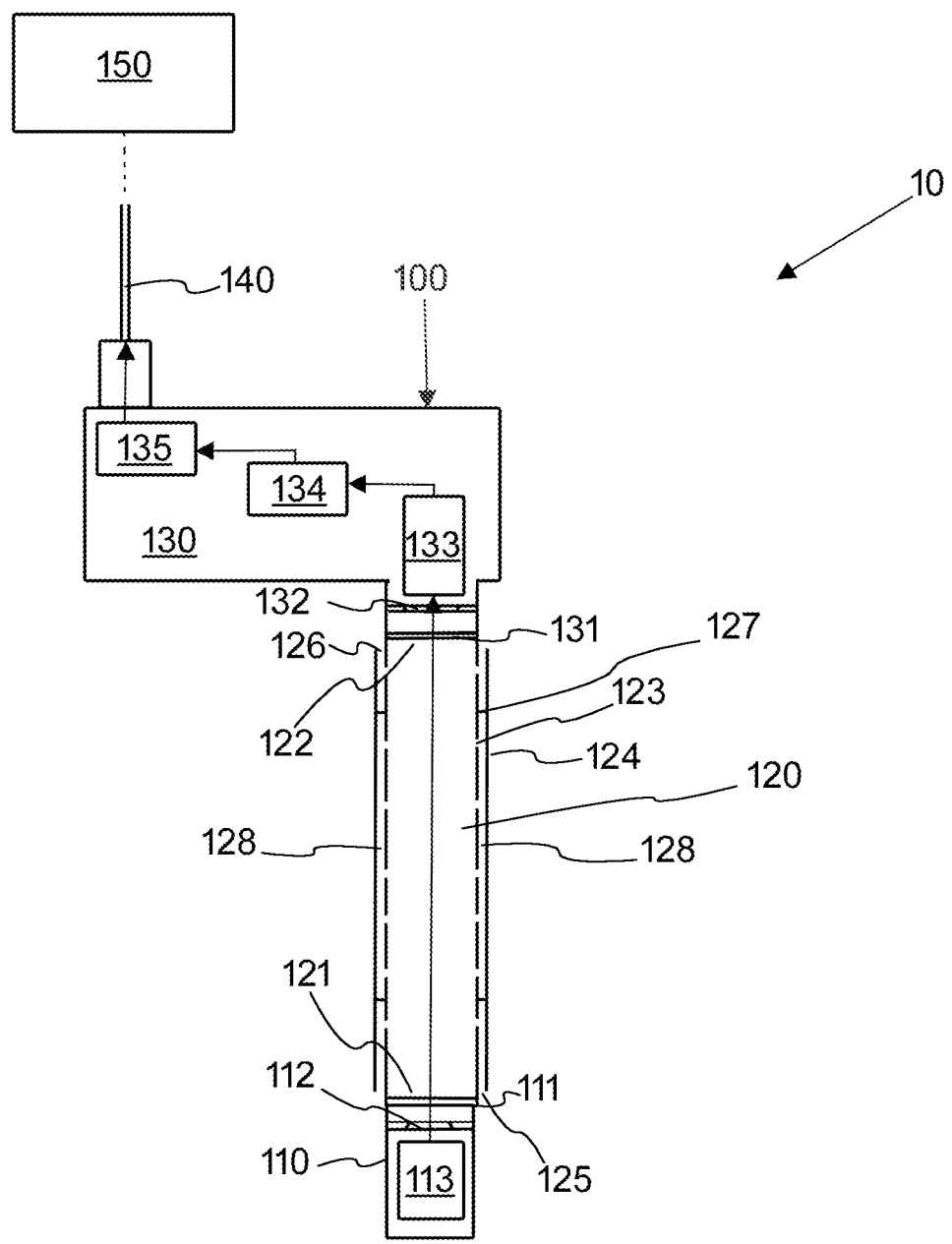

UNDERWATER ANALYSIS DEVICE FOR ANALYZING ABSORPTION CAPACITY OF WATER

TECHNICAL FIELD

The present invention relates to an underwater analysis device for analyzing absorption capacity of water after light is passed through it.

PRIOR ART

Water analysis under deep water provides obtaining important information related to the ingredient of water in this depth. Water analysis can be realized by means of carrying water to the surface physically and by means of analyzing with various methods here.

In the application with number U.S. Pat. No. 4,434,364A, a method is disclosed where light is applied to underwater and where the density of the components of the reflected light and where water is analyzed and where the hydrocarbon amount in water is detected. However, in order to be able to realize this method, a vehicle is needed which can move under the sea. Moreover, it is not possible to realize such examination in high depths about 5000 meters. Moreover, environmental factors and objects can manipulate light and this may lead to realizing erroneous measurements.

As a result, because of all of the abovementioned problems, an improvement is required in the related technical field.

BRIEF DESCRIPTION OF THE INVENTION

The present invention relates to an underwater analysis device, for eliminating the above mentioned disadvantages and for bringing new advantages to the related technical field.

An object of the present invention is to provide an underwater analysis device in order to provide making water analysis continuously in deep waters.

Another object of the present invention is to provide realization of water analysis in increased wavelength range.

In order to realize all of the abovementioned objects and the objects which are to be deducted from the detailed description below, the present invention is an underwater analysis device for analyzing absorption capacity of water. Accordingly, the subject matter device is characterized by comprising a body having a sealed first casing which accommodates a sealed illumination window; a sealed second casing which accommodates a sealed measurement window; a prismatic hollow water chamber provided between said first casing and said second casing and arranged such that a first inlet thereof faces said illumination window and such that a second inlet thereof faces said measurement window; said water chamber comprises pluralities water transfer openings; said first casing comprises a light emitting unit arranged to emit test light from the illumination window towards the measurement window; said second casing comprises a light sensing unit arranged to at least partially receive the test light passing through the water in the water chamber and to embody in a manner generating signal in accordance with the density of the received test light components. Thus, water analysis is provided in deep waters.

In a preferred embodiment of the present invention, a processor unit is provided which is positioned inside the second casing and embodied to generate signal related to the ingredient of water through which light is passed according to the signal generated by said light sensing unit.

In another preferred embodiment of the present invention, a communication unit is provided for providing transmission of the signal, received from said processor unit, to the outer devices.

In another preferred embodiment of the present invention, a sealed transmission line extends outwardly from said second casing.

In another preferred embodiment of the present invention, an outer jacket is provided in a manner encircling said water chamber; at least one connection wall is provided for connecting the water chamber and the outer jacket in a manner defining a water passage channel which provides connection of the outer medium and the water transfer openings in between. Thus, direct water input to the water transfer openings is prevented and thereby, clogging of the water transfer openings is at least partially prevented or the water transfer openings are at least partially prevented from being subject to a foreign object.

In another preferred embodiment of the present invention, said light emitting unit is embodied to emit light in the spectrum of 200 and 1100 nm. Thus, a wide spectrum is covered and the analysis scope is widened.

In another preferred embodiment of the present invention, said second casing comprises a first light refractor positioned between the illumination window and the light emitting unit.

In another preferred embodiment of the present invention, said second casing comprises a second light refractor positioned between the measurement window and the light sensing unit.

In another preferred embodiment of the present invention, said light emitting unit is embodied to emit normalized light.

BRIEF DESCRIPTION OF THE FIGURES

FIG. 1 is a representative schematic view of the underwater analysis device.

DETAILED DESCRIPTION OF THE INVENTION

In this detailed description, the subject matter is explained with references to examples without forming any restrictive effect only in order to make the subject more understandable.

With reference to FIG. 1, the subject matter underwater analysis device (10) comprises a first casing (110), a second casing (130) and a body (100) having a water chamber (120) provided between said first casing (110) and said second casing (130).

The first casing (110) has a leak-proof structure and comprises an illumination window (111). The illumination window (111) has a sealed structure. The illumination window (111) moreover at least partially comprises a transparent surface and thus, it permits light passage between the first casing (110) and the outer medium.

The first casing (110) comprises a light emitting unit (113). Said light emitting unit (113) is embodied to optionally emit test light in the predefined spectrum. In this exemplary embodiment, the light emitting unit (113) is embodied to emit light in the spectrum of 200 and 1100 nm.

The first casing (110) moreover comprises a first light refractor (112) positioned between the light emitting unit (113) and the illumination window (111). Said first light refractor (112) has a sealed structure. The first light refractor (112) provides the light, passing through it, to be made compliant for spectrophotometry and provides additional sealing.

The second casing (130) is provided in a sealed structure and comprises a measurement window (131). Said measurement window (131) has a sealed structure. The measurement window (131) at least partially comprises a transparent surface and thus, it permits light transfer between the second casing (130) and the outer medium. The second casing (130) also comprises a second light refractor (132).

The second casing (130) comprises a light sensing unit (133). Said light sensing unit (133) may comprise pluralities of photo-diodes for providing sensing of lights in different spectrums. The light sensing unit (133) may comprise pluralities of amplifiers (not illustrated in the figure) for amplifying the signals generated by photo-diodes. The light sensing unit (133) receives the signals generated by photo-diodes and related a processor unit (134) which estimates the ingredient of water according to the signal values and which generates signal in relation. The second casing (130) moreover comprises a communication unit (135). The communication unit (135) provides transfer of the signals generated by the processor unit (134) or the signals generated by the light sensing unit (133). The second casing (130) may be related to a transmission line (140). Said transmission line (140) is connected to the second casing (130) in a manner providing sealing. Thus, the signals generated by the processor unit (134) or the light sensing unit (133) can be transferred to the outer medium in a safe manner.

A water chamber (120) is provided between the first casing (110) and the second casing (130). The water chamber (120) is in the form of a hollow prism comprising a first inlet (121) and a second inlet (122). Said first inlet (121) and said second inlet (122) are provided mutually such that the light exiting one of them reaches the other one. In this exemplary embodiment, the water chamber (120) has a cylindrical form.

The first inlet (121) is connected to the illumination window (111) and the second inlet (122) is connected to the measurement window (131). The lateral surface of the water chamber (120) comprises pluralities of water transfer openings (123). Thus, water input to the inner gap of the water chamber (120) and water exit through this gap are permitted. The water chamber (120) is connected to an outer jacket (124) which encircles the lateral surface thereof. The diameter of the outer jacket (124) is greater than the diameter of the water chamber (120) such that a water passage channel (128) can be defined in between. Connection walls (127) are provided between the outer jacket (124) and the water chamber (120). The gap between the outer jacket (124) surface and the water chamber (120), in other words, the water passage channel (128) provides connection of the outer medium and the water transfer openings (123). The outer jacket (124) prevents liquid input with orthogonal angle to the water transfer openings (123) and it functions as a barrier in front of the water transfer openings (123). The water input through a first jacket inlet (125) and a second jacket inlet (126) passes through the water passage channel (128) and it reaches the water transfer openings (123) and from here, it reaches the inner opening of the water chamber (120).

The transmission line (140) can be connected to a user interface (150). Said user interface (150) provides displaying of the analysis results.

The subject matter, of which the details of an exemplary embodiment are given above, functions as follows:

The body (100) is placed under water. Water enters through the first jacket inlet (125) or through the second jacket inlet (126) and follows the water passage channel (128) and enters into the water chamber (120) through the water transfer openings (123) and fills the water chamber (120). Water enters into and exits the water chamber (120). Thus, the cycle of the analyzed water is provided. The light emitting unit (113) exits the illumination window (111) and it passes through the water inside the water chamber (120) and it provides spreading of the test light advancing towards the measurement window (131). The light sensing unit (133) partially receives the test light passing through water. The light sensing unit (133) generates measurement signal according to the density of the components of the sensed light. Said measurement signal is transmitted to the processor unit (134) and signal related to the ingredient of water is generated with respect to these signals by the processor unit (134). In more details, the measurement signal or the signal generated by the processor unit (134) can be displayed in a real-time manner on a user interface (150). The measurement signal or the signal generated by the processor unit (134) can be obtained in the form of a continuous graphic on the user interface (150). As the light components absorbed by water are detected, data can be obtained for examining the hydrocarbon distribution in water according to the absorbed wavelengths, for examining the bio-activity of water (algae capacity), for examining the plankton capacity of the water, for examining the soil particles in water in terms of erosion, for examining methane (bio-activity, examination of the fault lines), for examining water quality, for examining the saltiness proportion in a sensitive manner depending on the kind of the salt.

The protection scope of the present invention is set forth in the annexed claims and cannot be restricted to the illustrative disclosures given above, under the detailed description. It is because a person skilled in the relevant art can obviously produce similar embodiments under the light of the foregoing disclosures, without departing from the main principles of the present invention.

REFERENCE NUMBERS

10 Underwater analysis device
100 Body
110 First casing
   111 Illumination window
   112 First light refractor
   113 Light emitting unit
120 Water chamber
   121 First inlet
   122 Second inlet
   123 Water transfer opening
   124 Outer jacket
   125 First jacket inlet
   126 Second jacket inlet
   127 Connection wall
   128 Water passage channel
130 Second casing
   131 Measurement window
   132 Second light refractor
   133 Light sensing unit
   134 Processor unit
   135 Communication unit
140 Transmission line
150 User interface

What is claimed is:

1. An underwater analysis device for analyzing light absorption capacity of water, characterized by comprising a body having a sealed first casing which accommodates a sealed illumination window; a sealed second casing which accommodates a sealed measurement window; a prismatic hollow water chamber provided between said first casing and said second casing and arranged such that a first inlet thereof faces said illumination window and such that a second inlet thereof faces said measurement window; said water chamber comprises pluralities water transfer openings;

said first casing comprises a light emitting unit arranged to emit test light from the illumination window towards the measurement window;

said second casing comprises a light sensing unit arranged to at least partially receive the test light passing through the water in the water chamber said light sensing unit comprises pluralities of photodiodes for sensing light components in different spectrum in the test light and further the light sensing unit is configured in a manner generating signal in accordance with the density of the sensed test light components.

2. An underwater analysis device according to claim 1, wherein processor unit is provided which is positioned inside the second casing and embodied to generate signal related to the ingredient of water through which light is passed according to the signal generated by said light sensing unit.

3. An underwater analysis device according to claim 1, wherein a communication unit is provided for providing transmission of the signal, received from said processor unit, to the outer devices.

4. An underwater analysis device according to claim 1, wherein a sealed transmission line extends outwardly from said second casing.

5. An underwater analysis device according to claim 1, wherein an outer jacket is provided in a manner encircling said water chamber; at least one connection wall is provided for connecting the water chamber and the outer jacket in a manner defining a water passage channel which provides connection of the outer medium and the water transfer openings in between.

6. An underwater analysis device according to claim 1, wherein said light emitting unit is embodied to emit light in the spectrum of 200 and 1100 nm.

7. An underwater analysis device according to claim 1, wherein said second casing comprises a first light retractor positioned between the illumination window and the light emitting unit.

8. An underwater analysis device according to claim 1, wherein said second casing comprises a second light retractor positioned between the measurement window and the light sensing unit.

9. An underwater analysis device according to claim 1, wherein said light emitting unit is embodied to emit normalized light.

* * * * *